United States Patent [19]

Taub

[11] Patent Number: 4,820,630

[45] Date of Patent: Apr. 11, 1989

[54] ASSAY FOR NUCLEIC ACID SEQUENCES, PARTICULARLY GENETIC LESIONS, USING INTERACTIVE LABELS

[75] Inventor: Floyd Taub, Rockville, Md.

[73] Assignee: Digene Diagnostics, Incorporated, Md.

[21] Appl. No.: 674,190

[22] Filed: Nov. 23, 1984

[51] Int. Cl.$^4$ .......................... C12Q 1/68; C12Q 1/70; C12Q 1/28; C12Q 1/32

[52] U.S. Cl. .......................................... 435/5; 935/78; 436/501; 436/63; 436/800; 435/6; 435/803; 435/28; 435/26; 435/14

[58] Field of Search ..................... 435/5, 6, 7, 803, 13, 435/14, 15, 26, 27, 28, 259, 810, 436/501, 533, 800, 808, 811, 63, 503; 935/7, 9, 77, 78, 19

[56] References Cited

U.S. PATENT DOCUMENTS

| | | | |
|---|---|---|---|
| 4,358,535 | 11/1982 | Falkow et al. | 435/38 X |
| 4,374,925 | 2/1983 | Litman et al. | 436/800 X |
| 4,376,165 | 3/1983 | Hornby et al. | 435/7 X |
| 4,378,428 | 3/1983 | Farina et al. | 435/7 |
| 4,395,486 | 7/1983 | Wilson et al. | 436/504 X |
| 4,463,090 | 7/1984 | Harris | 435/7 |
| 4,486,539 | 12/1984 | Ranki et al. | 436/504 |
| 4,581,333 | 4/1986 | Kourilsky et al. | 435/6 |
| 4,656,127 | 4/1987 | Mundy | 935/78 X |
| 4,663,278 | 5/1987 | DiNello | 435/7 |
| 4,683,194 | 7/1987 | Saiki et al. | 935/9 X |

FOREIGN PATENT DOCUMENTS

| | | |
|---|---|---|
| 0070686 | 1/1983 | European Pat. Off. . |
| 0130515 | 1/1985 | European Pat. Off. . |
| 0137515 | 4/1985 | European Pat. Off. . |
| 0142299 | 5/1985 | European Pat. Off. . |
| 0144914 | 6/1985 | European Pat. Off. . |
| 0144913 | 6/1985 | European Pat. Off. . |
| 0147665 | 7/1985 | European Pat. Off. . |
| 0159719 | 10/1985 | European Pat. Off. . |
| 84/02721 | 7/1984 | World Int. Prop. O. . |
| 85/04663 | 10/1985 | World Int. Prop. O. . |

OTHER PUBLICATIONS

Renz, M. et al., *Nucleic Acids Research*, vol. 12, No. 8, Apr. 25, 1984, pp. 3435-3444.

Roninson, I. B. et al., *Nature*, vol. 309, Jun. 14, 1984, pp. 626-628.

*Chemical Abstracts*, vol. 98, No. 17, 1983, p. 280, Abstract No. 139894m, Patel, A. et al., "Chemiluminescence Energy . . . in Living Systems".

Cox, M. M. et al., *Proc. Natl. Acad. Sci. USA*, vol. 78, 1981, p. 3433.

Das Gupta, C. et al., *Proc. Natl. Acad. Sci. USA*, vol. 79, 1982, p. 762.

Bianchi, M. E. et al., *Cell*, vol. 35, 1983, p. 511.

Das Gupta, C. et al., *Cell*, vol. 22, 1980, p. 437.

Bianchi, M. et al., *Cell*, vol 34, 1983, p. 931.

B. Conner et al., *Proc. Natl. Acad. Sci. USA*, 80:278-282 (1983).

Orkin et al., *Chem. Abstracts*, 101:70382d (1984), p. 456.

Orkin et al., *Concise Report*, 64:311-313 (1984).

*Primary Examiner*—Johnnie R. Brown
*Assistant Examiner*—Jeremy M. Jay
*Attorney, Agent, or Firm*—Saidman, Sterne, Kessler & Goldstein

[57] ABSTRACT

Lesions in genetic sequences, for example, the sickle cell anemia mutation in the beta globin gene, are detected by means of interactive labels in a nucleic acid hybridization assay. A signal is generated only if the labels are in physical proximity which is made dependent on whether a predetermined normal or abnormal sequence is present by exposure to appropriate conditions such as restriction enzyme digestion or stringent hybridization.

25 Claims, No Drawings

ASSAY FOR NUCLEIC ACID SEQUENCES, PARTICULARLY GENETIC LESIONS, USING INTERACTIVE LABELS

BACKGROUND OF THE INVENTION

Embodiments of this invention were disclosed in Disclosure Documents No. 129,717, dated Aug. 2, 1984, recorded Aug. 6, 1984, and 130094, dated Aug. 14, 1984, recorded Aug. 17, 1984, incorporated by reference, which the Patent and Trademark Office is requested to preserve.

In the past, genetic diseases were diagnosed based on clinical findings once the disease had developed. Various enzyme and protein tests were subsequently developed to confirm or provide more accurate diagnosis and to allow earlier diagnosis. Unfortunately, for many diseases no such tests are available.

Recently, it has become possible to analyze an individual's DNA (which is present in every cell) to determine if certain abnormal genes which will cause genetic diseases are present. These diseases include Huntington chorea, phenylketonuria, thalassemias, and sickel cell anemia. The abnormal genes are found by analyzing restriction site polymorphisms (RSPs) using "Southern blotting" (SB) (Southern, E.M.S., Molecular Biology, 1975, 98:503). This test is time consuming and expensive. However, it is an extremely important method, since it has allowed prenatal diagnosis and thus intervention to prevent birth of severely diseased individuals.

Kan and Dozy, The Lancet 910 (Oct. 28, 1978) described a new approach to prenatal diagnosis of sickel cell anemia utilizing a "Southern blot" of DNA from amniotic fluid cells. When normal DNA was digested with the enzyme Hpa I, the beta-globin gene was contained in a 7.6 kb fragment. In variant DNA, the gene was found in fragments 7.0 kb (hemoglobin-A) or 13.0 kb (hemoglobin-S) in length. The polymorphic Hpa I site detected by this method was not located in the beta-globin gene itself, but rather in an adjacent sequence. Thus "this method of analysis is indirect and suitabe only in those cases where the parents at risk can be shown to carry the appropriate linked polymorphism prior to aminocentesis." Benz, Am. J. Ped. Hematol.-/Oncol. 6:59 (Spring 1984). (This was done by family studies.).

It is known that sickle cell anemia is caused by a single nucleotide base mutation in the beta globin gene which converts a glutamic acid codon (CAG) to one coding for valine (GTG). Nienhuis, N. Engl. J. Med. 299:195 (1978) proposed direct analysis by means of a restriction enzyme whose recognition site is created or eliminated by the point mutation. His candidate, Mnl I, yield small (60–80 bp) fragments that could not be resolved by blotting techniques at that time.

Wilson, et al., U.S. Pat. No. 4,395,486 (1983) found that direct diagnosis of sickle cell anemia was possible by restriction assay with an enzyme, such as Dde I, recognizing a CTNAG. The B-globin gene fragment was identified by a radiolabeled probe complementary to the 5' end of the gene. Individuals with normal hemoglobin had 175 bp and 201 bp bands; anemic individuals have a single 376 bp band. Unfortunately, the small Dde I generated fragments could be detected and distinguished only after sophisticated technical modification of the blotting techniques.

A new enzyme, Mst I, made possible the use of conventional techniques as directed in Wilson, el al., PNAS (USA) 79:3628 (June 1982). The normal fragment was 1.14 bp long, while sickle cell individuals produced a 1.34 kb fragment.

These fragments are separated according to size by gel electrophoresis. Since many other fragments from the non-globin DNA are also present, a special procedure ("Southern Blot") must be used to find the globin fragments. (Southern, PNAS [USA] 76: 3683–3687 [1979].) After electrophoresis, the DNA is transferred to a filter support (ex., nitrocellulose); then the filter is reacted with a radioactive probe which specifically binds to the globin sequences. This probe will stick to the globin sequences and, following washing and autoradiography, it can be determined whether the patient has 1.34 kb or 1.14 kb length fragments or both. The process of electrophoresis, transfer, filter hybridization, washing, and autoradiography are expensive, time consuming, and, for some size fragments, very difficult.

All of the aforementioned techniques for diagnosing SCA require that the disease create or destroy a restriction site.

Another approach permits one to detect single base changes (point mutations) in genomic DNA even where the change does not alter a restriction site. "Under appropriate hybridization conditions, only perfectly base-paired oligonucleotide-DNA duplexes will form; duplexes containing a single mismatched pair will not be stable." Conner, et al., PNAS (USA) 80:278 (January 1983). In this method, an oligonucleotide complementary to the DNA of a normal (or afflicted) individual in the affected region is synthesized, radiolabeled, and hybridized under stringent conditions. The duplexes are examined by autoradiography. Commenting on this approach, Orkin, BLOOD 63-249 (February 1984) writes: "In order to detect globin DNA fragments or other single-copy sequences in blot hybridization of total DNA, the synthetic probe must be rendered highly radioactive. Our own experience indicates that this is the most troublesome part of the methodology."

Thus, while more versatile than restriction mapping techniques, the stringent hybridization technique shares the disadvantageous requirements for radioactive probes, gel electrophoresis, Southern blotting, filter hybridization, washing and autoradiography. The present invention dispenses with these requirements.

It is known that radiolabelling of probes may be replaced by labeling with biotin, the biotin label then being detected by its affinity with avidin or its binding to an anti-biotin antibody (either then being linked to a reporter enzyme like peroxidase). Renz, EMBO J. 2:817 (1983). The art does not teach, however, use of interactive labels whose interaction is differentially affected by treatment depending on the sequences to which they are bound.

Falkow, U.S. Pat. No. 4,358,935 describes a method of diagnosing an infection utilizing a heterogeneous assay for pathogen DNA or RNA. The assay reagent is a labeled RNA or DNA probe. The patent states that "for the most part" the probe will be radiolabeled. It generaly alludes to the use of labels known in the immunoassay art, but without expression of any preference for a particular nonradioactive label or any discussion of interactive labels. Nor does it mention use of adjacent probes that are differently labeled.

Taber, EP Appl 114,668 discloses a family of DNA probes each of which hybridizes to a different region of a single chromosome of Salmonella bacteria. These probes are preferably radiolabeled, but also may be labeled with biotin. This reacts with avidin to which is bonded a fluorophore, an electron-dense compound, an antibody, or one member of a catalyst/substrate pair. While several probes are preferably used simultaneously, additively increasing the intensity of the resulting signal, there is no suggestion of any interaction among the multiple labels thus associated with the chromosomal DNA. The interactive labels of the present invention afford a much greater increase in sensitivity than that afforded by Taber's noninteractive multiple labels.

Peterson, WO 83/03260 describes a method of determining the polymorphism of human MHC alleles which, like that of Wilson, is dependent on the fractionation of restriction fragments by size. While it recognizes alternative to radioisotopic labels, such as enzymes, enzymatic substrates, co-factors, co-enzymes and luminescent substances, it does not refer to the use of interactive labels.

Ehrlich, EP Appl 84, 796 and Mach, EP Appl 103,960, both relate to HLA (human lymphocyte antigen complex) diagnostic typing based on restriction site polymorphism. As with Wilson, the DNA is restricted and fractionated prior to hybridization. The Mach references refers to alternatives to radiolabeling of hybridization probes, but not to the use of interactive labels.

Ullman, U.S. Pat. No. 3,996,345 teaches an immunoassay system utilizing a fluorescer-quencher pair. In one embodiment, the fluorescer is attached to a first receptor and the quencher to a second receptor for a polyepitopic ligand.

Maggio, U.S. Pat. No. 4,233,402 describes the use of enzyme immunoassay utilizing a reactant label conjugated to an analyte, and a single producing label conjugated to an antibody to said analyte, where the reactant labels acts on a precursor compound to generate a signal mediator which in turn directly or indirectly acts on the signal producing label to generate a signal. Maggio teaches that one label must be attached to the analyte and the other to the receptor. Thus, he teaches against the use of two interactively labeled probes or of a doubly interactively labeled probe. Finally, Maggio does not suggest that interactive label may be used to distinguish a normal DNA sequence from a mutated sequence, let alone suggest a means whereby the difference in sequence operates to affect the interaction of the labels.

Other immunoassay patents of interest are Litman, U.S. Pat. No. 4,275,149; Litman, U.S. Pat. No. 4,299,916; Zuk, U.S. Pat. No. 4,208,479; and Harris, U.S. Pat. No. 4,463,090. The Harris patent deals with cascade amplification of immunoassay signals.

These immunoassays are used to measure trace amounts of organic compounds, not to elucidate fine structure. If the aforestated assays are used to detect a ligand-receptor complex comprising a DNA probe hybridized to sample DNA, they will not be effectual at detecting the lesion. Since stringent hybridization conditions are not used, and the duplex is not cleaved between the labels, the presence or absence of the resulting signal is not dependent on the presence of the lesion. Generally speaking, these immunoassay techniques require special adaptation to detect the fine differences in nucleic acid sequence with which the present invention is concerned.

While the discussion herein focused on prenatal diagnosis of sickel cell anemia, the method of the present invention is equally applicable to other genetic disorders for which the locus of the lesion, and either the normal or mutated sequence about the lesion, are known or isolatable.

SUMMARY OF THE INVENTION

In the diagnostic method of this invention, sample cells are collected, their DNA is isolated, purified, denatured, and hybridized. The sample DNA and/or probe DNA are labeled. At least two labels are utilized, and these labels are chosen so that they cooperate, when in physical proximity, to yield a detectable signal. The labels are associated with the sample or probe DNA at locations such that their continued physical proximity is dependent on whether the sample DNA contains the lesion of interest.

These sequences may code for a protein, may regulate DNA expression, or otherwise be of interest. Lesions are single or multiple insertions, deletions or substitutions, i.e., mutations, of biological significance.

In another application of this invention, one may assay DNA for the degree of amplification of a particular sequence, such as a multi-drug resistance gene, in a cell. For example, Robinson, et al., Nature 309–626, 628 (June 1984) report that a 1.1 Kb fragment was strongly amplified in certain multi-drug resistant tumor cell lines. The level of the signal generated by the method of this invention would be indicative of the degree of amplification. In a simple modification of this procedure, the mRNA transcribed from said gene is assayed instead. This provides an indication of the degree of expression of the gene in question. One may assay for cellular and viral oncogenes and other tumor markers besides multi-drug resistance. Another use would be to assay for abnormal number of chromosomes by assaying for a gene normally present as a single copy. This would be of value in the diagnosis of Klinefelter's, Turner's, and Down's Syndromes, as well as other conditions associated with chromosomal abnormalities.

Still another use would be to determine the family relationship of two subjects by assaying for marker genes.

SOURCE OF SAMPLE DNA

Sample DNA may be isolated from cells present in the amniotic fluid, or from peripheral blood lymphocytes, as taught by Wilson, et al., U.S. Pat. No. 4,395,486 (1983) and others. Other convenient sources of DNA may be present in a particular situation and it is not intended that this invention be construed to be limited to any particular source or manner of isolating sample DNA.

SOURCE OF PROBE DNA

Probes may be prepared by conventional techniques, including chemical synthesis, reverse transcription from mRNA, or restriction-and isolation of DNA of known content or sequence. It is not intended that this invention be construed to be limited to any particular manner of preparing the probe.

The probe prepared is one having a sequence complementary to a region proximate to the lesion. By "proximate" is meant either "adjacent", or "including", or both, as may be desirable. Finally, the probe prepared may be complementary to either the coding or anticoding strand of the gene, as desired.

EXAMPLE OF LABELS

These may include but are not limited to enzymes, enzyme substrates, proenzymes, proenzyme activators (including cofactors and coenzymes), reagents to alter the microenvironment such as various polar or nonpolar or other chemicals or polymers, fluorescent labels, bioluminescent labels, or any other labels that may interact with each other to enhance, alter, or diminish a signal. In some situations it may be desirable to use more than two interactive labels (for example an enzyme cascade or chain might be used). In some instances it may be desirable to use more than two probes also. The density of the label of the probe, as well as its location may be varied.

A "label" may also be an "intrinsic" label, i.e., a property of the sample or probe DNA (or RNA) such as mass or charge which can affect a second label, e.g., the fluorescence polarization of a fluorescent label. See Huchzermeier, U.S. Pat. No. 4,476,228.

EXAMPLES OF SIGNALS

These may include but are not limited to:
A. Production of luminescent (including fluorescent) products.
B. Alteration of the luminescence (including amplitude, polarization, and other properties) of one label by the other.
C. Chemiluminescence.
D. Light absorbent (colored) products.
E. pH changes.
F. NMR changes.
G. Alteration in the absorption or emission of electromagnetic radiation by the label or other component, generally.
H. Gravimetric, volumetric, or electrochemical changes.
I. Precipitation or agglutination, generally.

The term "signal" is also used broadly herein to include the discontinuance of an existing signal.

A "signal" may constitute a rate of change in a detectable parameter rather than an absolute value of a parameter.

The signal may be monitored individually, automatically, or semi-automatically.

ATTACHMENT OF LABELS TO PROBES

The labels may be attached to the probes, directly or indirectly, by a variety of techniques. They may be covalently bound or held to the probe by a variety of associations. Depending on the precise type of labels used they might be located at the ends of the probes throughout the length of the probes or attached to linkers of various sizes and compositions to facilitate interactions. One form of attachment would be to label an antibody specific to a homopolymeric DNA strand, and utilize a probe having a homopolymeric tail. The label would then be attached to the probe by the antibody linker by antigen-antibody binding.

The label may be specifically attached to the probes following hybridization. In this case the probes might contain small tags, such as biotin or mercury and the specific labels would be attached selectively based on the affinity for these tags at any time even after hybridization. (The advantage of this system would be the minimization of steric hindrance of the hybridization reaction.) Additional bases, or other moieties, might be added to the ends of the probes (1) as sites of label attachment, (2) to facilitate the interaction by spatial or steric effects or (3) to help bring the labels together. For example a short sequence of complementary bases attached to the two probes might facilitate interaction of the labels after the probes were bound to the genomic DNA. The attraction of sequences attached to the labels would of course be kept below that required for stable binding in the absence of sample nucleic acid.

A preferred technique of labeling DNA is given by Renz and Kurz, Nucleic Acids Research 11:3435 (1984). They described the use of polyethylenimine as a cross linking agent to bind enzymes to DNA probes.

The size and composition of the DNA sequences (probes) to which the labels are attached will depend on the specific sequence being analysed.

DESCRIPTION OF THE SEVERAL EMBODIMENTS

In the first embodiment of the method of this invention, a first labeled probe, complementary to a region 5' of the site of interest, and a second labeled probe, complementary to a region 3' of the site of interest, are utilized. If the site constitutes a recognition/restriction site for an enzyme, digestion of the sample DNA with that enzyme and hybridization of the restriction fragments to the labelled probes will separate the two labels and thus hinder their interaction to produce a signal.

Many combinations of interactive labels are possible. In one preferred combination, the first label is the enzyme glucose oxidase, which, acting on a glucose substrate, generates hydrogen peroxide, and the second label is the enzyme horseradish peroxidase, which catalyzes the chemiluminescent reaction of the hydrogen peroxide with luminol. In a second preferred combination, one label is hexokinase and the other is glucose-6-phosphate dehydrogenase. Litman, et. al., Anal. Biochem. 106: 223-229 (1980). A number of useful enzymatic labels and reactions are taught in tables IV through VIII of Litman, U.S. Pat. No. 4,275,149 (1981).

It is not necessary to utilize two enzymatic labels. One label may be, for example, aminobutylethylisoluminol (ABEI), and the other fluorescein. The ABEI is a chemiluminescent substance which exhibits a spectral shift as a result of interaction with the fluorescein. Patel and Campbell, Clin. Chem. 29: 1604-1608 (1983).

In still another combination, the DNA probe is labeled with beta galactosidase, and macromolecular o-nitrophenyl-beta-galactoside, a positively charged substrate for that enzyme, is bound by electrical attraction to (negatively charged) sample DNA. The interaction of substrate and enzyme is detectable by monitoring the rate of increase in light scattering. Gibbons, et. al., Clin. Chem. 27: 1602-1608 (1981).

In a refinement of this method, a "scavenger" enzyme is used to hinder interaction between labels attached to unlinked DNA fragments. For example, the enzyme catalase may be used to destroy free hydrogen peroxide. Phosphorfructokinase may be used as a scavenger in the hexokinase system. Other methods of limiting diffusion of free components of the signal generating system or to diminish the signal generated by such components may be used.

In one embodiment of the method of the invention the first label is an enzyme which acts on a substrate to generate a messenger species which in turn interacts with a second label to generate a signal.

In another refinement of this method, a "cascade" of more than two enzymes may be used in the signal-generating system. Such multiple enzyme cascades, culminating in signal generation, are known from Harris, U.S. Pat. No. 4,463,090 where they are used in enzyme immunoassays.

In a second embodiment of this invention, a single, doubly-labelled probe is used which is complementary to the region of interest. The points of attachment of the first and second labels are then sufficiently far apart so as to be left on separate fragments if a restriction enzyme acts upon the mutated site.

In a third embodiment of this invention, a single labelled probe is used, but an interactive label is also attached to the sample DNA.

In a fourth embodiment of the invention, a single label is attached to the probe, or the sample DNA, and this label generates a signal which is altered upon hybridization. For example, the fluorescent polarization of a fluorescent-labeled probe may be altered when the probe is hyridized to the sample DNA.

In a fifth embodiment of this invention, interactive labels are utilized to assay point mutations which do not create or destroy a recognition/restriction site. One label is attached to an oligonucleotide complementary to the normal DNA sequence, and the other label is attached to the sample DNA or to another poly or oligonucleotide complementary to a proximate region of the sample DNA. As taught by Conner, et al., PNAS (USA) 80:278 (1983), under appropriate hybridization conditions the normal sequence will hybridize but the mutated sequence will not. Thus, the labels will interact effectively only if the sequences match perfectly.

The precise size and composition of the synthetic probes would depend on many factors including the specific sequence being analysed and any alterations in the formation and stability of the hybrids that might result from the attachment of labels or tags for label attachment.

As taught by Orkin, BLOOD 63:249 (February 1984), the hybridization conditions may be established with cloned mutant and normal genes and then extended to total genomic digests.

Of course, it is possible to utilize a probe which is complementary to the mutated rather than the normal sequence, in which case the signal is indicative of the genetic disorder.

In a sixth embodiment of this invention, an enzyme is utilized which preferentially attacks single stranded DNA, such as S1 nuclease or Mung-bean nuclease. (Brief descriptions of these enzymes may be found in Maniatis, Molecular Cloning 140-141, 1982.) If the probes are perfectly homologous to a region of the sample DNA, no point of attack is offered by the duplex. If, however, a mutation (deletion, insertion or substitution) prevents perfect binding, the nonhomologous regions would be attacked and cut. One might use a doubly labeled probe, the interacting labels 5' and 3', respectively, of the expected point of attack. Alternatively, one label could be placed on the probe, and the other on the sample DNA; or both labels could be placed on the sample DNA; so long as the labels would be on separate fragments if enzymatic attack was effective.

While the discussion above utilizes sample DNA and DNA probes by way of example, the methods of this invention may readily be adapted to the examination of sample RNA or the use of RNA probes.

While the methods of this invention are of great advantage in the detection of DNA lesions associated with genetic disorders, they may readily be adapted to the detection of the preservation or alteration of a predetermined sequence, and the term "gene" therefore should be read broadly. The method is not limited to human genes, but may be applied to the assay of nucleic acid sequences of human, animal, plant, microbial, or viral origin, whether natural or synthetic, for instance for diagnostic purposes. The sample nucleic acid may be attached to support means.

Although several embodiments of the invention have been described, it will be appreciated that many combinations, modifications and variations are possible in the light of the above teachings. It is, therefore, to be understood that this invention is not limited to the specific embodiments described.

I claim:

1. A method of detecting the presence or absence of a site for a restriction endonuclease enzyme, which comprises:
   (a) providing a sample nucleic acid to be detected for a site for a restriction endonuclease enzyme;
   (b) exposing said sample nucleic acid to a restriction endonuclease enzyme;
   (c) stably hybridizing said sample nucleic acid with
      (i) a first labeled nucleic acid probe capable of stably hybridizing to a region 5' to said site to be detected, and
      (ii) a second labeled nucleic acid probe capable of stably hybridizing to a region 3' to said site to be detected,
      the labels in said first and second nucleic acids probes together constituting a signal-generating system wherein said labels are in sufficient physical proximity so as to be capable of interacting with each other to yield a detectable signal when said site is absent but are in insufficient physical proximity so as to be less capable of yielding a detectable signal when said site is present; and
   (d) detecting said signal generating system, to thereby detect the presence or absence of said site.

2. The method of claim 1 wherein said step (b) occurs prior to said step (c).

3. The method of claim 1 wherein said step (c) occurs prior to said step (b).

4. A method of detecting the presence or absence of a site for a restriction endonuclease enzyme, which comprises:
   (a) providing a sample nucleic acid to be detected for a site for a restriction endonuclease enzyme;
   (b) stably hybridizing said sample nucleic acid with a doubly labeled nucleic acid probe capable of stably hydribizing to a region spanning said site when said site is absent, and carrying a first label at a position 5' to said site and a second label at a position 3' to said site;
   said first and second labels together constituting a signal generating system wherein said labels are in sufficient physical proximity so as to be capable of interacting with each other to yield a detectable signal when said site is absent but are in insufficient physical proximity so as to be less capable of yielding a detectable signal when said site is present;
   (c) exposing said sample nucleic acid to a restriction endonuclease enzyme; and (d) detecting said signal generating system, to thereby detect the presence or absence of said site.

5. A method of detecting the presence or absence of a region of biological significance in a nucleic acid sequence, which comprises:
(a) providing a sample nucleic acid sequence to be detected for the presence or absence of a region of biological significance in said sequence,
(b) incubating said sample nucleic acid with
  (i) a first labelled nucleic acid probe capable of stably hydridizing to said nucleic acid sequence when said region is absent, and
  (ii) a second labelled nucleic acid probe capable of stably hydribizing to a region proximate thereto;
wherein both said first and second labels are enzymes, and said labels interact by diffusion of a chemical species from one to another;
the enzymes in said first and second nucleic acid probes together constituting a signal generating system, wherein said enzymes are in sufficient physical proximity so as to be capble of interacting with each other to yield a detectable signal when said region of biological signficance is absent, but are in insufficient physical proximity so as to be less capable of yielding a detectable signal when said region of biological significance is present; and
(c) detecting said signal generating system to thereby detect the presence or absence of said region to biological significance.

6. A method of detecting the presence or absence of a region of biological signifance in a nucleic acid sequence, which comprises:
(a) providing a sample nucleic acid sequence to be detected for the presence or absence of a region of biological significance in said sequence,
(b) incubating said sample nucleic acid with
  (i) a first labelled nucleic acid probe capability of stably hydridizing to said nucleic acid sequence when said region is present, and
  (ii) a second labelled nucleic acid probe capable of stably hydridizing to a region proximate thereto;
wherein both said first and second labels are enzymes and said enzymes interact by diffusion of a chemical species from one to another;
the enzymes in said first and second nucleic acid probes together constituting a signal generating system, wherein said enzymes are in sufficient physical proximity so as to be capable of interacting with each other to yield a detectable signal when said region of biological significance is present, but are in insufficient proximity so as to be less capable of yielding a detectable signal when said region of biological significance is absent; and
(c) detecting said signal generating system to thereby detect the presence or absence of said region of biological significance.

7. A method of detecting the presence or absence of a site for a restriction endonuclease enzyme which comprises,
(a) providing a sample nucleic acid containing a site for a restriction endonuclease enzyme in a genetic sequence;
(b) labeling said sequence with a first label;
(c) exposing said sample nucleic acid to a restriction endonuclease enzyme;
(d) hybridizing said sample nucleic acid with a nucleic acid probe capable of stably hybridizing to the region spanning said site when said site is absent, said probe labeled with a second label,
said first and second labels together constituting a signal generating signal wherein said labels are in sufficient physical proximity so as to be capable of interacting with each other to yield a detectable signal when said site is absent, but are in insufficient physical proximity so as to be less capable of yielding a signal when said site is present; and
(e) detecting said signal generating system to thereby detect the presence or absence of said site.

8. The method of claim 7 wherein said step (c) occurs prior to said step (d).

9. The method of claim 1, 4 or 7 wherein said first label is a pro-enzyme activator which acts upon a pro-enzyme to yield an activated form, which interacts with said second label to generate a signal.

10. The method of claims 1, 4 or 7 wherein said first label is an enzyme which acts on a substrate to generate a messenger species, which in turn interacts with said second label to generate a signal.

11. The method of claim 10 wherein the interactive labels on the first and second probes are glucose oxidase and horseradish peroxidase or are hexokinase and glucose-6-phosphate dehydrogenase.

12. The method of claim 10 in which the signal generating system further comprises scavenger means operating on said messenger species to diminish its interaction with said label on said second probe.

13. The method of claim 12 wherein said scavenger is selected from the group consisting of catalase and phosphofructokinase.

14. The method of claims 1, 4 or 7 wherein said first label is a chemiluminescent substance and said second label is a fluorophore interacting therewith.

15. The method of claim 14 wherein said label on said first probe is aminobutylethylisoluminol.

16. The method of claims 1 4, or wherein said first label is an enzyme substrate and said second label is an enzyme acting on said substrate to generate a signal.

17. The method of claims 1, 4 or 7 wherein both said first and second labels are enzymes, and said labels interact by diffusion of a chemical species from one to another.

18. The method of claim 17 wherein said species is hydrogen peroxide.

19. The method of claims 1, 4, 7, 5 or 6 wherein said sample nucleic acid is obtained from a cell or a virus.

20. The method of claims 1, 4, 7, 79, or 80 wherein said sample nucleic acid is first attached to a support means.

21. The method of claims 1, 4 or 7, wherein said sample nucleic acid and said nucleic acid probe or probes are hybridized under conditions sufficiently stringent so that hybridization requires complete homology between said sample nucleic acid and said nucleic acid probe or probes.

22. A method of diagnosis of a genetic disorder of known genetic determination in a subject which comprises:
(a) obtaining cells from said subject,
(b) isolating nucleic acid from said cells bearing the gene whose normality is in question,
(c) distinguishing the normal gene from the abnormal gene by the method of claims 1, 4, 7, 5 or 6.

23. The method of claim 22 which is prenatal diagnosis, and wherein said cells are of fetal origin.

24. The method of claims 1, 4, or 7 wherein said first and second labels interact to enhance a signal.

25. The method of claims 1, 4 or 7, wherein said first and second labels interact to diminish an existing signal.

* * * * *

UNITED STATES PATENT AND TRADEMARK OFFICE
CERTIFICATE OF CORRECTION

PATENT NO. : 4,820,630

DATED : April 11, 1989

INVENTOR(S) : Floyd Taub

It is certified that error appears in the above-identified patent and that said Letters Patent is hereby corrected as shown below:

Claim 20, line 1, delete "79, or 80" and replace therefor --5 or 6--.

Signed and Sealed this

First Day of October, 1991

Attest:

HARRY F. MANBECK, JR.

*Attesting Officer*     *Commissioner of Patents and Trademarks*